US009918970B2

(12) United States Patent
Yoshioka et al.

(10) Patent No.: US 9,918,970 B2
(45) Date of Patent: Mar. 20, 2018

(54) PHARMACEUTICAL COMPOSITION COMPRISING SOLIFENACIN

(75) Inventors: Tatsunobu Yoshioka, Tokyo (JP); Makoto Murai, Tokyo (JP); Hiroaki Tasaki, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/110,295

(22) Filed: May 18, 2011

(65) Prior Publication Data
US 2011/0288118 A1 Nov. 24, 2011

Related U.S. Application Data

(60) Provisional application No. 61/346,311, filed on May 19, 2010.

(51) Int. Cl.
*A61K 31/435* (2006.01)
*A61K 47/32* (2006.01)
*A61K 31/439* (2006.01)
*A61K 47/48* (2006.01)

(52) U.S. Cl.
CPC ........... *A61K 31/439* (2013.01); *A61K 47/32* (2013.01); *A61K 47/48176* (2013.01); *A61K 47/48184* (2013.01)

(58) Field of Classification Search
USPC .............................................. 514/277, 772.4
See application file for complete search history.

(56) References Cited

U.S. PATENT DOCUMENTS

| | | | |
|---|---|---|---|
| 5,811,436 | A | 9/1998 | Leonard et al. |
| 6,017,927 | A | 1/2000 | Takeuchi et al. |
| 7,001,615 | B1 | 2/2006 | Singh et al. |
| 8,545,829 | B2 | 10/2013 | Mertin et al. |
| 2006/0177414 | A1* | 8/2006 | Mertin et al. ............ 424/78.12 |
| 2008/0039516 | A1 | 2/2008 | Sugihara et al. |
| 2008/0103171 | A1 | 5/2008 | Umejima et al. |

FOREIGN PATENT DOCUMENTS

| | | |
|---|---|---|
| CN | 1671361 A | 9/2005 |
| CN | 101141961 A | 3/2008 |
| JP | 2006-503806 | 2/2006 |
| KR | 20050010015 | 1/2005 |
| WO | 96/20194 A1 | 7/1996 |
| WO | 2006/070735 A1 | 7/2006 |
| WO | WO 2008/128028 | * 10/2008 |
| WO | WO 2008128028 | 10/2008 |

OTHER PUBLICATIONS

Patent Examination Report No. 1 issued in Australian Patent Application No. 2011255951, dated Jun. 28, 2013 in the name of Astellas Pharma Inc.

The State Intellectual Property Office of the People's Republic of China, Notification of the Second Office Action in Application No. 201180024741.8, date of issuing: May 21, 2014 with English Translation.
The Eurasian Patent Organization, First Official Office Action in Application no. 201291276, date of issuing May 30, 2014 with English Translation.
Office Action dated Mar. 13, 2014, issued by the Mexican Institute of Industrial Property (IMPI) in corresponding Patent application No. MX/a/2012/013328.
L. Hughes, "New Uses of Ion Exchange Resins in Pharmaceutical Formulation", Rohm and Haas Research Laboratories—Spring House, 5 pages, 2004.
Chinese Office Action issued in Chinese Application No. 201180024741.8, issued Sep. 9, 2013.
Extended European Search Report issued in European Application No. 11783576.9, issued Oct. 18, 2013.
Weinreb et al., "A Novel Formulation of an Ophthalmic Beta-Adrenoceptor Antagonist", Journal of Parenteral Science & Technology, 1992, 46(2):51-53; XP009172621.
Li et al., "Utilization of a Modified Special-Cubic Design and an Electronic Tongue for Bitterness Masking Formulation Optimization", Journal of Pharmaceutical Sciences, 2007, 96(10):2723-2734; XP055079581.
Hughes, "Ion Exchange Resinates—The Technology Behind the Mystery". Pharmaceutical Technology Europe, 2005, 17(4):38-42; XP002713056.
Anand et al., "Ion-exchange resins: carrying drug delivery forward", Drug Discovery Today, 2001, 6(17):905-914; XP001127363.
Ayenew et al., "Trends in Pharmaceutical Taste Masking Technologies: A Patent Review", Recent Patents on Drug Delivery & Formulation, 2009, 3(1):26-39; XP055020918.
"Viscosity of Carbopol Polymers inAqueous Systems", Lubrizol, 2009, p. 1-10; XP002713057.
Office Action, issued in Ukranian Application No. 201214528, issued Jul. 3, 2015.
Office Action, issued in corresponding KR Application No. 10-2012-7033019, dated Sep. 7, 2015.
Office Action, issued in corresponding MX Application No. MX/a/2012/013328, dated Aug. 4, 2015.
Examination Report dated Oct. 14, 2015 for IL Patent Application No. 223113 (English translation).
Chun et al., "Preparation and Characterization of Enrofloxacin/Cabopol Complex in Aqueous Solution," Arch. Pharm. Res., 2004, vol. 27, No. 6, pp. 670-675.
Lubrizol—Compendial Specifications Applicable to Carbopol and Pemulen Pharmaceutical-Grade Polymers Based on Individual Monographs, 2013. (Appendix A).
Lubrizol—Typical Properties of Carbopol Polymers and Pemulen Pharmaceutical-Grade Polymers, 2013, pp. 1-3. (Appendix B).
Communication Pursuant to Article 94(3) EPC, Application No. 11 783 576.9-1464, dated Dec. 9, 2014.
Mexican Institute of Industrial Property (IMPI) Second Office Action in Application No. MX/a/2012/013328 dated Dec. 1, 2014 with English Translation.

(Continued)

*Primary Examiner* — Shobha Kantamneni
(74) *Attorney, Agent, or Firm* — McCarter & English, LLP; Maria Laccotripe Zacharakis; Sai Venkatesh Seetharaman

(57) ABSTRACT

Disclosed is a pharmaceutical composition comprising a complex between solifenacin or a pharmaceutically acceptable salt thereof and an ion exchange resin, and an acrylic based polymer.

6 Claims, No Drawings

(56) References Cited

OTHER PUBLICATIONS

Office Action, issued in Chinese Application No. 201180024741.8, dated Feb. 2, 2015.
Office Action, issued in Eurasian Application No. 201291276, dated Jan. 22, 2015.
Office Action, issued in Japanese Application No. 2012-515902, dated Jan. 13, 2015.
Office Action, issued in corresponding CA Application No. 2,799,942, dated Jun. 13, 2017.

* cited by examiner

PHARMACEUTICAL COMPOSITION COMPRISING SOLIFENACIN

CROSS-REFERENCE TO RELATED APPLICATIONS

This Application claims the benefit of U.S. Provisional Patent Application No. 61/346,311, filed May 19, 2010, the disclosure of which is incorporated herein by reference in its entirety.

TECHNICAL FIELD

The present invention relates to a pharmaceutical composition containing solifenacin or a pharmaceutically acceptable salt thereof. More particularly, the present invention relates to a pharmaceutical composition containing a complex between solifenacin or a pharmaceutically acceptable salt thereof and an ion exchange resin, and an acrylic based polymer.

BACKGROUND ART

Solifenacin is represented by the following structural formula and its chemical name is (R)-quinuclidin-3-yl (S)-1-phenyl-1,2,3,4-tetrahydroisoquinoline-2-carboxylate.

[Chemical 1]

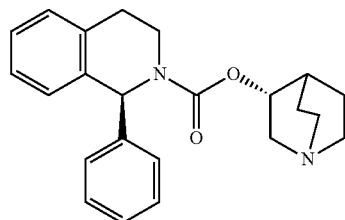

It has been reported that solifenacin or a salt thereof has an excellent selective antagonistic activity against muscarinic $M_3$ receptor and is useful as a preventive or a therapeutic agent for urologic diseases such as urinary incontinence and pollakiuria in nervous pollakiuria, neurogenic bladder, nocturnal enuresis, unstable bladder, bladder spasms, chronic cystitis, and the like; respiratory diseases such as chronic obstructive lung diseases, chronic bronchitis, asthma, and rhinitis; and gastrointestinal diseases such as irritable bowel syndrome, spastic colitis, and diverticulitis (see patent literature 1).

In particular, this compound has higher selectivity for the $M_3$ receptor existing in the smooth muscle, gland tissues, or the like as compared with the $M_2$ receptor existing in the heart or the like, so that it has high utility as an $M_3$ receptor antagonist having less side effects on the heart or the like, particularly as a preventive agent or a therapeutic agent for urinary incontinence, pollakiuria, chronic obstructive lung diseases, chronic bronchitis, asthma, rhinitis, and the like. Solifenacin is currently sold in the form of a succinate salt as a therapeutic agent for urinary urgency, pollakiuria, and urge urinary incontinence due to overactive bladder under the name of Vesicare (registered trademark) in Japan [VESIcare (registered trademark) in the U.S. and Vesicare (registered trademark) in the Europe].

Currently available preparations are an oral solid preparation (tablet) and an orally disintegrating tablet, and from the standpoint of the compliance of patients, development of various dosage forms such as a liquid has been demanded. However, solifenacin and a salt thereof have very high solubility in various solvents and have very strong bitterness and astringency. In particular, in order to develop an oral liquid formulation, it was necessary to mask the bitterness and astringency.

For example, as a technique for masking the bitterness and astringency of the drug in an oral liquid formulation, forming complexes between the drug and an ion exchange resin has been known (see, for example, non patent literature 1 and patent literature 2). However, further improvement was needed for providing the oral liquid formulation of solifenacin.

Incidentally, as one of the techniques for producing a pharmaceutical composition which contains amorphous solifenacin and has improved stability, a solid pharmaceutical composition having an ion exchange resin blended therein has been disclosed (patent literature 3).

CITATION LIST

Patent Literature

[patent literature 1] U.S. Pat. No. 6,017,927 (corresponding to WO 96/20194)

[patent literature 2] U.S. Pat. No. 5,811,436

[patent literature 3] WO 2008/128028

Non Patent Literature

[non patent literature 1] Dr. L. Hughes, "New Use of Ion Exchange Resins in Pharmaceutical Formulation" (Rohm & Haas Research laboratories)

SUMMARY OF INVENTION

Technical Problem

The invention relates to a pharmaceutical composition containing a complex between solifenacin or a pharmaceutically acceptable salt thereof and an ion exchange resin, and provides a pharmaceutical composition which has good uniformity and dispersibility during and after production, which also has good drug content uniformity even without shaking or with gentle shaking when it is taken out from a container at the time of taking it, and which does not cause bitterness and astringency at the time of taking it and has an improved compliance.

Solution to Problem

The present inventors made intensive studies in order to develop a pharmaceutical composition of suspension (suspension liquid) which has reduced bitterness and astringency derived from solifenacin and has good drug content uniformity even without shaking or with gentle shaking when it is formed into a pharmaceutical composition of suspension. As a result, they found that a preparation which has good drug content uniformity during and after production and does not release the drug in the oral cavity and shows good release of the drug in the stomach can be obtained by adding a specific polymer to a suspension of complex between solifenacin and an ion exchange resin and adjusting the pH, and thus, the invention has been completed.

That is, the invention provides the following [1] to [10].

[1] A pharmaceutical composition containing a complex between solifenacin or a pharmaceutically acceptable salt thereof and an ion exchange resin, and an acrylic based polymer.

[2] The pharmaceutical composition according to [1], wherein the solifenacin or a pharmaceutically acceptable salt thereof is solifenacin succinate.

[3] The pharmaceutical composition according to [1] or [2], wherein the ion exchange resin is a cationic exchange resin.

[4] The pharmaceutical composition according to [3], wherein the cationic exchange resin is one or more members selected from the group consisting of polacrilin potassium, sodium polystyrene sulfonate, and polacrilex resin.

[5] The pharmaceutical composition according to any one of [1] to [4], wherein the acrylic based polymer is one or more members selected from the group consisting of Carbomer Homopolymer Type A, Carbomer Homopolymer Type B, Carbomer Homopolymer Type C, Carbomer 934, Carbomer 934P, Carbomer 941, and Carbomer 940.

[6] The pharmaceutical composition according to [5], wherein the acrylic based polymer is Carbomer Homopolymer Type A or Carbomer Homopolymer Type B.

[7] The pharmaceutical composition according to any one of [1] to [6], wherein the pH is about 5 or higher and about 9 or lower.

[8] The pharmaceutical composition according to any one of [1] to [7], wherein the pH is about 6 or higher and about 7 or lower.

[9] The pharmaceutical composition according to any one of [1] to [8], wherein the pharmaceutical composition is a suspension.

[10] The pharmaceutical composition according to [9], wherein the suspension is a preparation for oral administration.

Advantageous Effects of Invention

In the invention, by adding an acrylic based polymer to a suspension of complex between solifenacin or a pharmaceutically acceptable salt thereof and an ion exchange resin, particles of the complex can be uniformly dispersed in a suspension. Since the dispersion stability is improved, the composition can be easily packaged in bottles without causing a variation in the concentration at the time of production, and therefore, the invention has an effect that the productivity is improved and the production equipments are simplified. Further, at the time of administration, a suspension can be made uniform without shaking or with gentle shaking, and therefore, the invention has an effect that the accuracy and ease of dosage are improved. Further, since the acrylic based polymer does not form a gel under an acidic condition, the drug release from the ion exchange resin is not inhibited in the stomach, and therefore, the invention has an effect that delay or inhibition of drug absorption in the body is not caused.

DESCRIPTION OF EMBODIMENTS

Hereinafter, the pharmaceutical composition of the invention will be explained.

The term "to be uniformly dispersed" as used herein is defined as, for example, to be packaged in a bottle without causing a variation in the concentration at the time of production; as another embodiment, to show a good drug content uniformity after shaking a bottle filled with a suspension (suspension liquid); or as still another embodiment, not to cause a visually observed precipitation even after a bottle filled with a suspension (suspension liquid) is left for 1 hour.

The wording "dispersion stability is improved" as used herein is defined as the fact that the concentration of the drug taken out from an upper portion of a suspension (suspension liquid) in the bottle left for 1 week is, for example, 50% or more; as another embodiment, 70% or more; or as still another embodiment, 90% or more; when the drug concentration in the suspension (suspension liquid) filled in the bottle is regarded as 100%.

The wording "a drug is rapidly released" as used herein is defined as, for example, the fact that a drug release from an ion exchange resin is not inhibited in the stomach, and therefore, delay or inhibition of drug absorption in the body is not caused; or as another embodiment, the fact that 85% or more of the drug is released in 15 minutes in a dissolution test described in the United States Pharmacopeia using 0.1 N hydrochloric acid as a fluid for dissolution test.

Solifenacin or a pharmaceutically acceptable salt thereof to be used in the invention can be easily obtained by performing production by or in accordance with the production process described in WO 96/20194.

Solifenacin can form pharmaceutically acceptable salts with any of a broad range of inorganic and organic acids. Such salts also constitute a part of the present invention. Examples of such salts include acid addition salts with a mineral acid such as hydrochloric acid, hydrobromic acid, hydroiodic acid, sulfuric acid, nitric acid, or phosphoric acid; and those with an organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, or glutamic acid. As another embodiment, a succinate salt can be exemplified. These salts can be produced by a common procedure.

The dosage of the pharmaceutical composition of the invention is suitably determined according to the individual case in consideration of administration route, disease symptoms, age, gender, and the like of a subject in need of administration. When solifenacin succinate is administered, the dosage of the active ingredient is generally from about 0.01 mg/kg to 100 mg/kg per day per adult in the case of oral administration, and this dosage is administered once a day or in two to four divided doses a day. Further, in the case where intravenous administration is performed depending on the symptoms, solifenacin succinate is administered at a dosage ranging from 0.01 mg/kg to 10 mg/kg per administration per adult once or several times per day.

The blending amount of solifenacin is not particularly limited as long as it is a therapeutically or preventively effective amount. Such a blending amount is, for example, 85% by weight or less of the total amount of the preparation, as another embodiment, it is 80% by weight or less, as still another embodiment, it is 50% by weight or less, and as still further another embodiment, it is 10% by weight or less. Further, the concentration of solifenacin in a suspension (suspension liquid) is, for example, about 0.1 mg/mL or more and about 10 mg/mL or less, as another embodiment, it is about 0.2 mg/mL or more and about 5 mg/mL or less, as still another embodiment, it is about 0.2 mg/mL or more and about 4 mg/mL or less, and as still another embodiment, it is about 0.5 mg/mL or more and about 2 mg/mL or less. Alternatively, it is about 0.3 mg/mL or more and about 2 mg/mL or less.

The ion exchange resin is not particularly limited as long as it can form a complex with solifenacin, thereby reducing the bitterness and astringency derived from solifenacin and forming a pharmaceutically acceptable pharmaceutical composition. Specifically, for example, a pharmaceutically acceptable cationic exchange resin or anionic exchange resin can be exemplified. As another embodiment, a cationic exchange resin can be exemplified. Examples of the cationic exchange resin include a cross-linked polymer of methacrylic acid and divinylbenzene (a weakly acidic salt is formed from a carboxylic acid functional group of the methacrylic acid and potassium) (product name: Amberlite (registered trademark) IRP88, Dow Chemical Company, polacrilin potassium NF), a cross-linked polymer of styrenesulfonic acid and divinylbenzene (a strongly acidic salt is formed from a sulfonic acid group of the styrenesulfonic acid and sodium) (product name: Amberlite (registered trademark) IRP69, Dow Chemical Company, sodium polystyrene sulfonate USP), and a cross-linked polymer of methacrylic acid and divinylbenzene (product name: Amberlite (registered trademark) IRP64, Dow Chemical Company, Polacrilex Resin). As still another embodiment, Amberlite (registered trademark) IRP88 can be exemplified. As the ion exchange resin or cationic exchange resin, one kind can be used alone or two or more kinds can be used appropriately in combination in suitable amounts.

The blending amount of the ion exchange resin is not particularly limited as long as the amount permits the formation of a complex with solifenacin, thereby reducing the bitterness and astringency derived from solifenacin and forming a pharmaceutically acceptable pharmaceutical composition. Specifically, the blending amount of the ion exchange resin is, for example, about 0.1 mg/mL or more and about 50 mg/mL or less, as another embodiment, it is about 0.2 mg/mL or more and about 25 mg/mL or less, and as still another embodiment, it is about 0.5 mg/mL or more and about 4 mg/mL or less. Further, the blending amount ratio by weight of solifenacin to the ion exchange resin is from about 1:0.2 to about 1:10, as another embodiment, it is from about 1:0.5 to about 1:5, as still another embodiment, it is from about 1:1 to about 1:3, and as still another embodiment, it is from about 1:1 to about 1:2.

The acrylic based polymer is not particularly limited as long as it is a pharmaceutically acceptable acrylic based polymer and the viscosity thereof is increased by neutralization with an alkaline agent. Specific examples thereof include Carbopol 71G, 971P, 974P, 980, 981, 5984, ETD 2020, Ultrez 10, 934, 934P, 940, 941, 1342, and the like, and Pemulen TR-1, TR-2 and the like (available from Lubrizol); AQUPEC HV-501, HV501E, HV-501ER, HV-504, HV-504E, HV-505, HV-505E, HV-505ED, and the like (available from Sumitomo Seika Chemicals Co., Ltd.); and Hibiswako 103, 104, 105, and the like (available from Wako Pure Chemical Industries, Ltd.). As another embodiment, Carbopol 974P, 934, 934P, 971P, 941, 940, 910, and the like can be exemplified. As still another embodiment, Carbopol 974P (USP/NF Monograph for Carbomer Homopolymer Type B) and 971P (USP/NF Monograph for Carbomer Homopolymer Type A) can be exemplified. As the acrylic based polymer, one kind can be used alone or two or more kinds can be used appropriately in combination in suitable amounts.

The blending amount of the acrylic based polymer is not particularly limited as long as the amount permits the reduction in precipitation of the drug-ion exchange resin complex in the suspension. Specifically, the blending amount of the acrylic based polymer is, as one embodiment for example, about 0.5 mg/mL or more and about 10 mg/mL or less, as another embodiment, it is about 1 mg/mL or more and about 5 mg/mL or less, as still another embodiment, it is about 1.5 mg/mL or more and about 3 mg/mL or less, and as still another embodiment, it is about 2 mg/mL or more and about 3 mg/mL or less, although it is suitably determined according to the amount of the drug or ion exchange resin, the type of polymer, the amount of the alkaline agent, the pH, or the like.

The viscosity of the acrylic based polymer can be adjusted by appropriately adding an alkaline agent and/or a pH adjuster to acrylic based polymer in suitable amounts, and the viscosity of the pharmaceutical composition (suspension, suspension liquid) of the invention.

Examples of the alkaline agent which neutralizes the acrylic based polymer to cause gelation include inorganic bases such as sodium hydroxide, potassium hydroxide, and ammonium hydroxide; and organic bases such as triethanolamine, L-arginine, tromethamine, aminomethyl propanol, and tetrahydroxypropyl ethylenediamine. As the alkaline agent, one kind can be used alone or two or more kinds can be used appropriately in combination in suitable amounts.

Examples of the pH adjuster include various acids such as citric acid, acetic acid, hydrochloric acid, succinic acid, tartaric acid, malic acid, phosphoric acid, boric acid, fumaric acid, ascorbic acid, glutamic acid, as well as the alkaline agent.

A suitable pH is not particularly limited as long as it is in a range that allows the acrylic based polymer to swell so as to increase the viscosity. Specifically, the pH is, for example, about 5 or higher and about 9 or lower, as another embodiment, it is about 5 or higher and about 8 or less, as still another embodiment, it is about 6 or higher and about 7 or lower, and as still another embodiment, it is about 6.0 or higher and about 6.9 or lower. Incidentally, as shown in Test Example 1 described later, when the pH is about 5 or higher and about 9 or lower, the pH is in a range that allows solifenacin and the ion exchange resin to sufficiently form a complex, and therefore, the bitterness and astringency derived from solifenacin in the suspension can be masked.

A suitable viscosity of the suspension (suspension liquid) is not particularly limited as long as it is in a range that a complex of the drug with an ion exchange resin is uniformly dispersed in the suspension and dispersion stability is improved. The range is, for example, 100 cPs or more and 8000 cPs or less as another embodiment, 130 cPs or more and 5000 cPs or less as still another embodiment, and 150 cPs or more and 3000 cPs or less as still another embodiment, when the viscosity is determined at 25° C. using a rotational viscometer (Brookfield digital viscometer, Model: LVDV-II+) at 100 rpm.

The pharmaceutical composition of the invention is formulated into a preparation by suitably using any of a variety of pharmaceutical excipients as needed. Such a pharmaceutical excipient is not particularly limited as long as it is a pharmaceutically acceptable and pharmacologically acceptable excipient, and for example, a preservative, a corrigent, a flavor, a dispersant, a humectant, a buffer, an antifoaming agent, a solvent, or the like is used.

As the preservative, methyl parahydroxy benzoate, ethyl parahydroxy benzoate, propyl parahydroxybenzoate, butyl parahydroxy benzoate, benzoic acid, benzyl alcohol, sorbic acid, acetic acid, or a salt thereof can be blended.

As the corrigent, a sugar or a sugar alcohol such as sucrose, fructose, lactose, sorbitol, mannitol, xylitol, erythritol, or trehalose; or a sweetening agent such as aspartame, acesulfame potassium, sucralose, neotame, or saccharin can be blended.

As the flavor, for example, lemon, lemon lime, orange, menthol, strawberry, banana, raspberry, bubble gum flavor, or the like can be blended.

As the humectant, a polyoxyethylene sorbitan fatty acid ester such as polysorbate 80 or Arlacel 83; a polyoxyethylene hydrogenated castor oil such as HCO-50; or a surfactant such as a sugar ester can be blended.

As the dispersant or thickener, locust bean gum, guar gum, pullulan, xanthane gum, carrageenan, tragacanth gum, dextrin, pectin, gelatin, or the like can be blended. Other than these additives, a nonionic substance can be blended as needed.

As the buffer, citric acid, phosphoric acid, boric acid, succinic acid, fumaric acid, tartaric acid, ascorbic acid, or a salt thereof, glutamic acid, glutamine, glycine, aspartic acid, alanine, arginine, or a salt thereof, magnesium oxide, zinc oxide, magnesium hydroxide, or a salt thereof, or the like can be blended.

As the antifoaming agent, simethicone, dimethicone, or the like can be blended. As the solvent, glycerin, propylene glycol, or the like can be blended.

As the pharmaceutical excipient, one kind can be used alone or two or more kinds can be used appropriately in combination in suitable amounts.

Hereinafter the production method of the invention will be explained.

The production method of the invention includes the steps comprising, for example, (1) a step of dissolving solifenacin, (2) a step of forming a complex between solifenacin and an ion exchange resin, and (3) a step of preparing a suspension (suspension liquid).

(1) Dissolution Step:

The drug is dissolved in a water-soluble solvent capable of dissolving the drug, whereby a drug solution is obtained. As the water-soluble solvent, water or an aqueous solution of an organic solvent capable of being arbitrarily dissolved in water such as a monohydric alcohol (such as methyl alcohol, ethyl alcohol, or isopropanol) or a ketone (such as acetone or methyl ethyl ketone), glycerin, propylene glycol, or the like can be exemplified.

(2) Complex Formation Step:

A reaction between the drug and an ion exchange resin is performed by adding an ion exchange resin to the drug solution obtained by dissolving the drug in the water-soluble solvent, followed by stirring. In this case, the ion exchange resin is preferably used in an amount about 1 to 5 times as much as that of the drug. The temperature during the reaction is not particularly limited, however, the reaction is preferably performed at room temperature. The reaction time is from about 0.5 to 6 hours. By the reaction, a drug-ion exchange resin complex in which the drug is adsorbed in an amount of about 80% or more of the theoretical ion adsorption amount can be quantitatively obtained, and above all, the complex is preferably used as a complex in which the drug is adsorbed in an amount of about 85% or more and about 100% or less of the theoretical ion adsorption amount.

(3) Dispersion or Suspension Step:

An acrylic based polymer is added to water or a solution obtained by adding, to water, an organic solvent capable of being arbitrarily dissolved in water and dispersed therein while stirring. At this time, another pharmaceutically acceptable additive may be added to water or the solution in advance. Further, it is also possible to mix the acrylic based polymer with another pharmaceutically acceptable additive in advance. The temperature at the time of dispersing the acrylic based polymer is not particularly limited, however, the acrylic based polymer is preferably dispersed at room temperature or if necessary, at a temperature lower than room temperature. Specifically, for example, the temperature is from 0° C. to 40° C., and as another embodiment, it is from 5° C. to 30° C. The dispersion time is, for example, from 0.5 hour to 24 hours, and as another embodiment, it is from 1 hour to 12 hours. While stirring the liquid in which the acrylic based polymer is dispersed, an alkaline agent is added thereto to increase the pH thereof, whereby the viscosity of the liquid is increased. The addition amount of the alkaline agent at this time is not particularly limited as long as the pH of the resulting liquid is in a range that allows the viscosity to increase. However, the addition amount of the alkaline agent is determined by considering the increase in the pH value after adding the drug-ion exchange resin complex. The drug-ion exchange resin complex is dispersed in the water-soluble solvent to which the acrylic based polymer and the pharmaceutically acceptable additive have been added.

As the pharmaceutical composition of the invention, the suspension obtained in the dispersion or suspension step described in the above (3) may be used as such, or the suspension is packaged in a capsule by a method known per se, and can also be used as a capsule preparation. Alternatively, from the complex obtained in the above (2), the solvent is evaporated by a method known per se, thereby preparing a dry composition (powder). Then, the resulting dry substance is formulated into a preparation such as a granule, a powder, a dry syrup, a pill, a tablet, or a capsule by a method known per se, and the preparation in such a dosage form can also be formulated as a ready-to-suspend preparation which is used by being resuspended in a solvent (preferably containing the acrylic based polymer) when it is taken. Alternatively, from the suspension obtained in the above (3), the solvent is evaporated by a method known per se, thereby preparing a dry composition (powder). Then, the resulting dry substance is formulated into a preparation such as a granule, a powder, a dry syrup, a pill, a tablet, or a capsule by a method known per se, and the resulting preparation is used, or the preparation in such a dosage form can also be formulated as a ready-to-suspend preparation which is used by being resuspended in a solvent when it is taken.

EXAMPLES

Hereinafter, the invention will be more specifically described with reference to Examples, Comparative Examples, and Test Examples, however, it should not be construed that the invention is limited to these.

Example 1

In a liquid obtained in advance by dispersing Carbomer Homopolymer Type B (Carbopol 974P NF, Lubrizol, hereinafter abbreviated as "Carbomer") in purified water, xylitol, acesulfame potassium, a paraben, and propylene glycol were dissolved. After the resulting liquid was neutralized with a sodium hydroxide solution, a complex obtained by reacting solifenacin succinate with polacrilin potassium (Amberlite IRP-88, Dow Chemical Company; the same product was used unless otherwise specified.) in purified water, an orange flavor, and a 30% simethicone emulsion were added thereto, and the pH of the resulting mixture was adjusted to 6.0, and the final concentration of each component was adjust with purified water to the desired value shown in Table 1. The unit in the table is mg/mL.

TABLE 1

| | Example (mg/mL) | | | | | | | |
|---|---|---|---|---|---|---|---|---|
| | 1 | 2 | 3 | 4 | 5 | 6 | 7 | 8 |
| Solifenacin succinate | 1 | 1 | 1 | 1 | 1 | 1 | 1 | 1 |
| Polacrilin potassium | 2 | 2 | 2 | 2 | 2 | 2 | 2 | 2 |
| Carbomer (Carbopol 974P NF) | 2 | 2 | 2 | 2 | 1.6 | 1.8 | 2 | 2 |
| 30% Simethicone emulsion | 3 | 3 | 3 | 3 | 3 | 3 | 3 | 3 |
| Methyl paraben | 1.6 | 1.6 | 1.6 | 1.6 | 1.6 | 1.6 | 1.6 | 1.6 |
| Propyl paraben | 0.2 | 0.2 | 0.2 | 0.2 | 0.2 | 0.2 | 0.2 | 0.2 |
| Propylene glycol | 20 | 20 | 20 | 20 | 20 | 20 | 20 | 20 |
| Xylitol | 150 | 150 | 150 | 150 | 150 | 150 | 150 | 150 |
| Acesulfame potassium | 0.51 | 0.51 | 0.51 | 0.51 | 0.51 | 0.51 | 0.51 | 0.51 |
| Orange flavor | 5 | 5 | 5 | 5 | 5 | 5 | 4 | 5 |
| Sodium hydroxide (4% aqueous solution) | q.s. | q.s. | q.s. | q.s. | q.s. | q.s. | q.s. | q.s. |
| Citric acid (10% aqueous solution) | q.s. | q.s. | q.s. | q.s. | q.s. | q.s. | q.s. | q.s. |
| Purified water | q.s. | q.s. | q.s. | q.s. | q.s. | q.s. | q.s. | q.s. |
| pH | 6 | 6.3 | 6.6 | 6.9 | 6.3 | 6.3 | 6.3 | 6.3 |

| | Example (mg/mL) | | | | | | | |
|---|---|---|---|---|---|---|---|---|
| | 9 | 10 | 11 | 12 | 13 | 14 | 15 | 16 |
| Solifenacin succinate | 0.5 | 1 | 1 | 1 | 0.5 | 1 | 1 | 1 |
| Polacrilin potassium | 1 | 2 | 2 | 2 | 1 | 2 | 2 | 2 |
| Carbomer (Carbopol 974P NF) | 2 | 2 | 2 | 2 | 3 | 3 | 3 | 3 |
| 30% Simethicone emulsion | 3 | 3 | 3 | 3 | 3 | 3 | 3 | 3 |
| Methyl paraben | 1.6 | 1.6 | 1.6 | 1.6 | 1.6 | 1.6 | 1.6 | 1.6 |
| Propyl paraben | 0.2 | 0.2 | 0.2 | 0.2 | 0.2 | 0.2 | 0.2 | 0.2 |
| Propylene glycol | 20 | 20 | 20 | 20 | 20 | 20 | 20 | 20 |
| Xylitol | 150 | 150 | 150 | 150 | 150 | 150 | 150 | 150 |
| Acesulfame potassium | 0.51 | 0.51 | 0.51 | 0.51 | 0.51 | 0.51 | 0.51 | 0.51 |
| Orange flavor | 10 | 10 | 10 | 10 | 10 | 10 | 10 | 10 |
| Sodium hydroxide (4% aqueous solution) | q.s. | q.s. | q.s. | q.s. | q.s. | q.s. | q.s. | q.s. |
| Citric acid (10% aqueous solution) | q.s. | q.s. | q.s. | q.s. | q.s. | q.s. | q.s. | q.s. |
| Purified water | q.s. | q.s. | q.s. | q.s. | q.s. | q.s. | q.s. | q.s. |
| pH | 6.3 | 5.4 | 6.4 | 7.0 | 6.3 | 5.2 | 6.3 | 7.0 |

| | Example (mg/mL) | | | |
|---|---|---|---|---|
| | 17 | 18 | 19 | 20 |
| Solifenacin succinate | 2 | 4 | 1 | 0.5 |
| Polacrilin potassium | 4 | 8 | 2 | 1 |
| Carbomer (Carbopol 974P NF) | 3 | 3 | — | — |
| Carbopol 971P NF | — | — | 10 | 5 |
| 30% Simethicone emulsion | 3 | 3 | — | — |
| Methyl paraben | 1.6 | 1.6 | — | — |
| Propyl paraben | 0.2 | 0.2 | — | — |
| Propylene glycol | 20 | 20 | — | — |
| Xylitol | 150 | 150 | — | — |
| Acesulfame potassium | 0.51 | 0.51 | — | — |
| Orange flavor | 10 | 10 | — | — |
| Sodium hydroxide (4% aqueous solution) | q.s. | q.s. | q.s. | q.s. |
| Citric acid (10% aqueous solution) | q.s. | q.s. | q.s. | q.s. |
| Purified water | q.s. | q.s. | q.s. | q.s. |
| pH | 6.4 | 6.5 | 6.0 | 6.2 |

Examples 2 to 7

Suspension liquids of the invention were produced based on the formulations shown in Table 1 in accordance with the production method described in Example 1.

Example 8

In the formulation of Example 2, Carbomer and a portion of xylitol were mixed in advance and dispersed in purified water. Xylitol, acesulfame potassium, a paraben, and propylene glycol were dissolved, and after the resulting liquid was neutralized, a complex obtained by reacting solifenacin succinate with polacrilin potassium in purified water, an orange flavor, and a 30% simethicone emulsion were added thereto. Then, the pH of the resulting mixture was adjusted to 6.3, and the final concentration of each component was adjust with purified water to the desired value shown in Table 1, whereby a suspension liquid of the invention was produced. The unit in the table is mg/mL.

Examples 9 to 18

After xylitol and acesulfame potassium were dissolved in purified water, Carbomer was dispersed in this solution, and a paraben and propylene glycol were dissolved in this dispersion. To the resulting liquid, an orange flavor, a 30% simethicone emulsion, a complex obtained by reacting solifenacin succinate with polacrilin potassium in purified water were added, and the pH of the resulting mixture was adjusted using a sodium hydroxide solution. The final concentration of each component was adjust with purified water to the desired value shown in Table 1. The unit in the table is mg/mL.

Carbomer Homopolymer Type A (Carbopol 971P NF, Lubrizol) was dispersed in purified water in advance. A complex obtained by reacting solifenacin succinate with polacrilin potassium in purified water was added to this dispersion, and the pH of the resulting liquid was adjusted using a sodium hydroxide solution. The final concentration of each component was adjust with purified water to the desired value shown in Table 1. The unit in the table is mg/mL.

Comparative Example 1

Light anhydrous silicic acid, xylitol, acesulfame potassium, and a 30% simethicone emulsion were suspended or dissolved by stirring with a homogenizer. After a paraben, hypromellose 2208 (Methocel K4M, Dow Chemical Company), propylene glycol, and glycerin were dissolved, a complex obtained by reacting solifenacin succinate with polacrilin potassium in purified water and an orange flavor were added thereto. Then, the pH of the resulting mixture was adjusted to 7.0, and the final concentration of each component was adjust with purified water to the desired value shown in Table 2, whereby a suspension liquid of Comparative Example was produced. The unit in the table is mg/mL.

Comparative Example 2

After crystalline cellulose/carmellose sodium (Avicel RC-591, FMC BioPolymer) was suspended in purified water by stirring with a homogenizer, xylitol and acesulfame potassium were added thereto and dissolved therein. After a paraben, propylene glycol, and glycerin were dissolved therein, a complex obtained by reacting solifenacin succinate with polacrilin potassium in purified water, an orange flavor, and a 30% simethicone emulsion were added thereto. Then, the pH of the resulting mixture was adjusted to 7.0, and the final concentration of each component was adjust with purified water to the desired value shown in Table 2, whereby a suspension liquid of Comparative Example was produced. The unit in the table is mg/mL.

Comparative Example 3

After Avicel RC-591 was suspended in purified water by stirring with a homogenizer, xylitol and acesulfame potassium were added thereto and dissolved therein. After a paraben, hypromellose 2208, propylene glycol, and glycerin were dissolved therein, a complex obtained by reacting solifenacin succinate with polacrilin potassium in purified water, an orange flavor, and a 30% simethicone emulsion were added thereto. Then, the pH of the resulting mixture was adjusted to 7.0, and the final concentration of each component was adjust with purified water to the desired value shown in Table 2, whereby a suspension liquid of Comparative Example was produced. The unit in the table is mg/mL.

TABLE 2

| | Comparative Example (mg/mL) | | |
|---|---|---|---|
| | 1 | 2 | 3 |
| Solifenacin succinate | 1 | 1 | 1 |
| Polacrilin potassium | 2 | 2 | 2 |
| Hypromellose 2208 (Methocel K4M) | 5 | — | 1 |
| Light anhydrous silicic acid | 10 | — | — |
| Crystalline cellulose/carmellose sodium (Avicel RC-591) | — | 12 | 15 |
| 30% Simethicone emulsion | 1 | 1 | 1 |
| Methyl paraben | 1.6 | 1.6 | 1.6 |
| Propyl paraben | 0.2 | 0.2 | 0.2 |
| Glycerin | 58.34 | 58.34 | 58.34 |
| Propylene glycol | 20 | 20 | 20 |
| Xylitol | 150 | 150 | 150 |
| Acesulfame potassium | 0.51 | 0.51 | 0.51 |
| Orange flavor | 4 | 4 | 4 |
| Sodium hydroxide (4% aqueous solution) | q.s. | q.s. | q.s. |
| Citric acid (10% aqueous solution) | q.s. | q.s. | q.s. |
| Purified water | q.s. | q.s. | q.s. |
| pH | 7.0 | 7.0 | 7.0 |

Test Example 1

Solifenacin succinate and an ion exchange resin (polacrilin potassium: IRP-88 or sodium polystyrene sulfonate: IRP-69, Dow Chemical Company) were reacted to each other for 1 hour in a solution of each pH at a weight ratio from 1:1 to 1:4, or 1:3 to 1:4. Then, the reaction mixture was centrifuged, and the amount of the drug contained in the supernatant was quantitatively determined. The amount of unbound drug is shown in Table 3 and Table 4, expressed as a percentage to the addition amount of the drug. In each case, when the pH was 5 or higher, solifenacin succinate and the ion exchange resin sufficiently formed a complex.

TABLE 3

| Drug:IRP-88 | pH 4 | pH 5 | pH 6 | pH 7 | pH 8 |
|---|---|---|---|---|---|
| 1:1 | 57.5 | 4.8 | 8.3 | 4.9 | 4.0 |
| 1:2 | 28.3 | 1.3 | 3.5 | 2.0 | 4.4 |
| 1:3 | 19.9 | 1.0 | 1.4 | 1.7 | 3.2 |
| 1:4 | 7.4 | 1.0 | 1.3 | 1.6 | 2.0 |

TABLE 4

| Dmg:IRP-69 | pH 4 | pH 5 | pH 6 | pH 7 | pH 8 |
|---|---|---|---|---|---|
| 1:3 | 3.5 | 1.0 | 4.0 | 1.6 | 2.3 |
| 1:4 | 1.4 | 0.7 | 0.7 | 0.8 | 1.4 |

Test Example 2

The prepared suspension (suspension liquid) was packaged in a bottle and left as such for 1 hour. Then, the presence or absence of a precipitate in the suspension at the bottom of the bottle was visually observed. The result is shown in Table 5. In all the suspensions (suspension liquids) of the Examples of the invention, a precipitate of the complex after the suspensions were left as such for 1 hour was not observed. On the other hand, in the case of Comparative Example in which Carbomer was not blended, a precipitate of the complex was observed.

TABLE 5

| | Presence or absence of precipitate (after 1 hour of being left as such) |
|---|---|
| Comparative Example 1 | Presence |
| Example 1 | Absence |
| Example 2 | Absence |
| Example 3 | Absence |
| Example 4 | Absence |
| Example 5 | Absence |
| Example 6 | Absence |
| Example 7 | Absence |
| Example 8 | Absence |
| Example 9 | Absence |
| Example 10 | Absence |
| Example 11 | Absence |
| Example 12 | Absence |
| Example 13 | Absence |
| Example 14 | Absence |
| Example 15 | Absence |
| Example 16 | Absence |
| Example 17 | Absence |
| Example 18 | Absence |

Test Example 3

The suspension (suspension liquid) was packaged in a bottle, and the bottle was left as such for a given period of time. Then, a sample of the drug suspension was taken out from an upper portion in the bottle, and the drug concentration was quantitatively determined by HPLC. The measurement result of the drug concentration is shown in Table 6, expressed as a percentage by taking the concentration of each formulation shown in Table 1 as 100%. In the case of Comparative Example 1, the drug concentration in the upper portion of the drug suspension after the drug suspension was left as such for 1 hour and 24 hours was decreased to 55.9% and 12.3%, respectively. On the other hand, in the case of the Examples of the invention, a precipitate was not formed or a slight precipitation was observed, even after 1 week (Table 6). Moreover, in the case of Example 7, the drug concentration in the upper portion of the drug suspension was not decreased (102.9%) even after 2 weeks. Therefore, it was shown that in the suspension (suspension liquid) of the invention, a uniform drug concentration can be maintained for a long period of time, and its good dispersion stability was confirmed.

TABLE 6

| | After 0 hour | After 1 week |
|---|---|---|
| Example 1 | 99.0% | 98.8% |
| Example 2 | 99.2% | 99.7% |
| Example 3 | 98.9% | 98.3% |
| Example 4 | 98.8% | 100.1% |
| Example 6 | 99.2% | 98.4% |
| Example 8 | 97.8% | 97.2% |
| Example 11 | 98.9% | 103.1% |
| Example 12 | 101.2% | 101.1% |
| Example 14 | 98.5% | 96.8% |
| Example 15 | 99.5% | 101.3% |
| Example 16 | 97.8% | 99.9% |
| Example 17 | 99.9% | 100.1% |
| Example 18 | 99.8% | 98.2% |

Test Example 4

Five mL of each suspension (suspension liquid) was added to 900 mL of 0.1 N hydrochloric acid, and a dissolution test was performed by the paddle method at a paddle speed of 50 rpm, and a dissolution rate after 15 minutes was determined. The result is shown in Table 7. All the suspensions of the invention showed a dissolution rate of 85% or more after 15 minutes of the dissolution test, and therefore, it was confirmed that the suspension of the invention is a preparation that can provide rapid dissolution in the same manner as a common solid preparation. From the results of Examples 10, 11, and 12 showing that rapid dissolution was observed at the range between about pH5.4 and about pH7.0, it was assumed that pH did not affect a dissolution rate in each formulation of these Examples. Further, it was revealed from the results of Examples 11 and 15 that rapid dissolution was achieved even in the case of an increased concentration of Carbomer. Furthermore, it was revealed from the results of Examples 15 and 18 that rapid dissolution was achieved even when the drug concentration varied.

TABLE 7

| | Dissolution rate after 15 min |
|---|---|
| Comparative Example 2 | 78% |
| Comparative Example 3 | 82% |
| Example 2 | 95% |
| Example 7 | 92% |
| Example 10 | 91% |
| Example 11 | 93% |
| Example 12 | 93% |
| Example 15 | 90% |
| Example 18 | 88% |

Test Example 5

A viscosity was determined at 25° C. using a rotational viscometer (Brookfield digital viscometer, Model:LVDV-II+) at 100 rpm. The result is shown in Table 8. An appropriate spindle was selected in accordance with the viscosity of each suspension (suspension liquid).

TABLE 8

| | Spindle | Viscosity (cPs) |
|---|---|---|
| Example 1 | LV3 | 196 |
| Example 2 | LV3 | 212 |
| Example 3 | LV3 | 220 |
| Example 4 | LV3 | 206 |
| Example 6 | LV3 | 138 |
| Example 8 | LV3 | 184 |
| Example 9 | LV3 | 328 |
| Example 10 | LV2 | 116 |
| Example 11 | LV3 | 216 |
| Example 12 | LV3 | 204 |
| Example 13 | LV4 | 1686 |
| Example 14 | LV3 | 522 |
| Example 15 | LV3 | 987 |
| Example 16 | LV3 | 980 |
| Example 17 | LV3 | 538 |
| Example 18 | LV3 | 236 |
| Example 20 | LV4 | 2244 |

INDUSTRIAL APPLICABILITY

In a pharmaceutical composition containing a complex between solifenacin or a pharmaceutically acceptable salt thereof and an ion exchange resin, the present invention can provide a pharmaceutical composition which has good uniformity and dispersibility during and after production, which also has good drug content uniformity even without shaking or with gentle shaking when it is taken out from a container at the time of taking it, and which does not cause bitterness at the time of taking it and has an improved drug compliance.

As above, the present invention was explained with reference to particular embodiments, but modifications and improvements obvious to those skilled in the art are included in the scope of the present invention.

What is claimed is:

1. A pharmaceutical composition comprising a complex between solifenacin or a pharmaceutically acceptable salt thereof and polacrilin potassium, and Carbomer Homopolymer Type B, wherein the pharmaceutical composition is
a rapid release suspension in which the complex is uniformly dispersed in water, and a water soluble liquid solvent comprising the Carbomer Homopolymer Type B, and the pH of the suspension is 5.4 to 7.0; and wherein the blending amount ratio by weight of solifenacin to polacrilin potassium is from 1:2 to 1:4, and the viscosity of the suspension is from 116 cPs to 987 cPs, when the viscosity is determined at 25° C. using a rotational viscometer at 100 rpm, and, wherein the blending amount ratio by weight of the Carbomer Homopolymer Type B to solifenacin or a pharmaceutically acceptable salt thereof and polacrilin potassium is 0.25 to 1.

2. The pharmaceutical composition according to claim 1, wherein the pH is between about 6 and about 7.

3. The pharmaceutical composition according to claim 1, wherein the suspension is a preparation for oral administration.

4. The pharmaceutical composition according to claim 1, wherein the concentration of the Carbomer Homopolymer Type B in water, and the water soluble liquid solvent is from 1.6 mg/ml or more to 3 mg/ml or less.

5. The pharmaceutical composition according to claim 1, wherein 85% or more of solifenacin is released in 15 minutes in a dissolution test performed by the paddle method at a paddle speed of 50 rpm wherein the fluid for the dissolution test is 0.1 N hydrochloric acid.

6. The pharmaceutical composition according to claim 1, wherein the water soluble liquid solvent is one or more members selected from the group consisting of propylene glycol, or glycerin.

* * * * *